United States Patent [19]

Moreno

[11] 4,028,930

[45] June 14, 1977

[54] MULTIPLE HOLDER FOR DETERMINING HEMATOCRIT

[76] Inventor: Enrique Moreno, Box 1750, Mayaguez, P.R. 00708

[22] Filed: Apr. 8, 1976

[21] Appl. No.: 675,163

[52] U.S. Cl. .................................. 73/61.4; 23/259; 73/427; 206/443

[51] Int. Cl.² .......................................... G01N 33/16

[58] Field of Search ............. 23/259, 292; 73/61.4, 73/427; 233/26; 206/379, 443

[56] References Cited

UNITED STATES PATENTS

| | | | |
|---|---|---|---|
| 2,261,423 | 11/1941 | Toulouse | 206/443 X |
| 2,737,312 | 3/1956 | Hamlon | 220/375 |
| 2,741,913 | 4/1956 | Dovas | 73/61.4 |
| 2,919,796 | 1/1960 | Pressl | 206/379X |
| 3,176,504 | 4/1965 | Shapiro | 73/61.4 |
| 3,319,780 | 5/1967 | Russell | 206/379 X |
| 3,812,707 | 5/1974 | Proni et al. | 73/61.4 |
| 3,824,841 | 7/1974 | Bull | 23/230 B X |

Primary Examiner—Morris O. Wolk
Assistant Examiner—Arnold Turk
Attorney, Agent, or Firm—Scrivener, Parker, Scrivener and Clarke

[57] ABSTRACT

For the determination of hematocrit percent in blood samples a tubular body is provided having an annular series of elongated container holes for receiving a plurality of blood samples after which the device is subjected to centrifugal force to separate the red cells from plasma. The device is transparent and a scale is marked on it so that the hematocrit percent can be read directly.

1 Claim, 3 Drawing Figures

MULTIPLE HOLDER FOR DETERMINING HEMATOCRIT

BACKGROUND OF THE INVENTION

The volume occupied by red cells in a unit of blood is expressed as a percentage known as the hematocrit percent, and must be measured in many diagnostic medical procedures. The measurement is usually performed by separating the red cells from plasma by subjecting a column of blood to centrifugal force. The invention provides a new and useful apparatus for receiving a plurality of columns of blood which is readily adapted to positioning in a centrifuge and which has readily viewable means for directly reading the hematocrit percent.

SUMMARY OF THE INVENTION

Figure 1:
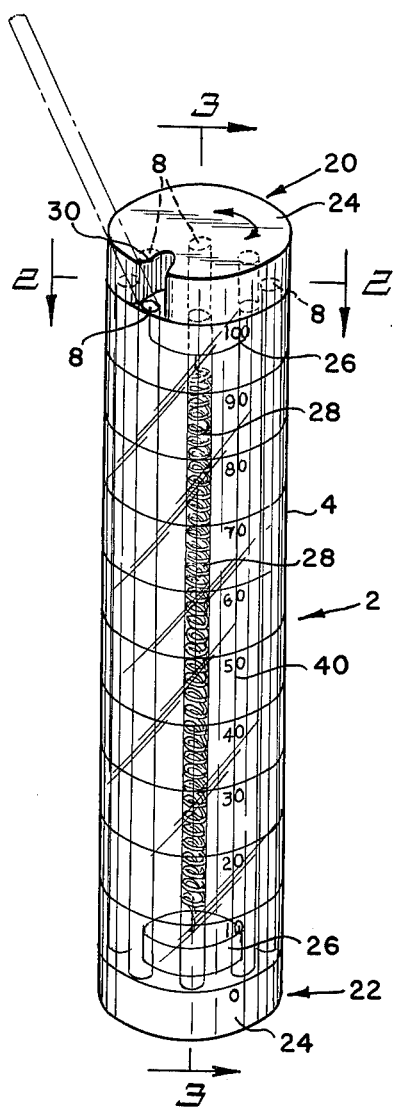
FIG. 1 is a perspective view of the holder for blood samples provided by the invention.
Figure 2:
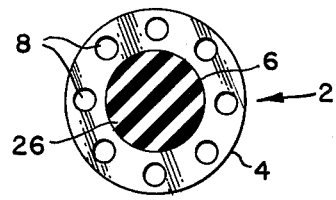
FIG. 2 is a transverse sectional view taken on line 2–2 of FIG. 1.
Figure 3:
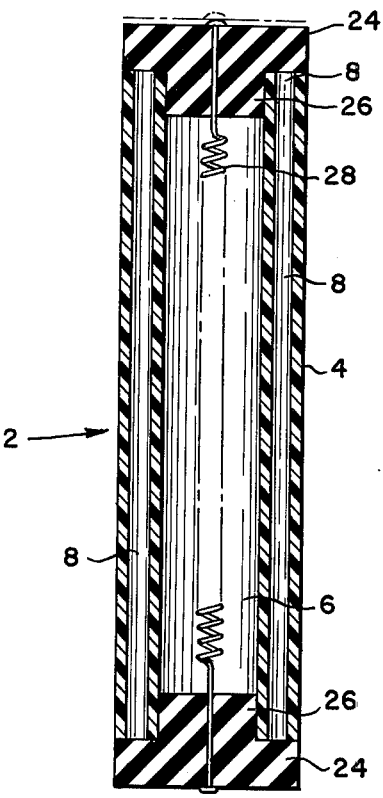
FIG. 3 is a longitudinal sectional view taken on line 3–3 of FIG. 1.

An elongated annular body is provided having formed therein an annular series of elongated holes each of which is a container within which a blood sample may be placed. The ends of the body and the holes therein are closed by heads which are connected by resilient means which hold the heads tightly against the ends of the body and permit rotation of at least one of the heads to cause an opening in that head to uncover the end of any container hole to permit introduction of blood into the hole and removal therefrom. The body is formed of transparent material and a scale extending along the body provides means for direct reading of hematocrit percent.

DESCRIPTION OF THE INVENTION

The holder for a plurality of blood samples comprises an elongated device 2 of cylindrical shape having an annular body part 4 of substantial thickness surrounding a central opening 6. Within the body part there are formed a plurality of elongated holes 8 which extend parallel to each other in an annular series and which constitute a plurality of containers each of which is adapted and intended to receive a blood sample. The holes are preferably open at one end and closed at the other, but may be open at both ends, and the cylindrical body may be of the order of 3 to 4 inches in length and ½ to 1 inch in diameter, but these dimensions are not critical.

Means are provided for closing the ends of the cylindrical body and the open end or ends of the container holes, and such means comprise two preferably rubber heads 20, 22 each of which has an outer circular part 24 which has the same outer diameter as the cylindrical body 4 and an inner circular part 26 which is of such diameter that it is snugly but movably received within the central opening 6. These two heads are connected by a spring or other resilient means 28 which extends longitudinally through the central opening 6 and which normally holds the heads in tight engagement with the ends of the cylindrical body 4 but permits one or both of the heads to be moved with respect to its adjacent end of the cylindrical body in order to allow the introduction of blood samples into the container holes 8.

In order to permit such introduction at least one of the heads 20, 22 is provided with a slot or opening 30 adjacent its periphery and extending inwardly of the head beyond the container holes 8. The head 20 may be rotated with respect to the cylindrical body 4 to successively uncover the container hole for the successive introduction of blood samples into them, and when the desired number of samples are in place the head is moved to a position in which the ends of all of the container holes are closed by the heads, after which the entire device is subjected to centrifugal force.

The annular body 4 is made of a transparent material which may be a synthetic plastic, glass or the like through which the blood samples are clearly visible, and one or more scales 40 is marked on the exterior surface of the annular body and extends longitudinally of it from end to end of the container holes 8. Each scale preferably consists of eleven equally spaced numerals ranging from 0 to 100 by tens and provides means for direct reading of the hematocrit percent after centrifuging.

The holder according to the invention may be made in either disposable or re-usable forms, and also may be made in various sizes. A preferred embodiment which has been found to be very useful has more than twenty container holes.

I claim:

1. A device for receiving and holding a plurality of blood samples for centrifuging to determine hematocrit percent, comprising an elongated transparent annular body defining a central open-ended opening, a plurality of elongated holes formed in the body and arranged in an annular series within the body and extending longitudinally thereof and each having at least one open end, a head at each end of the annular body normally closing the central opening and the ends of the holes, resilient means extending through the central opening and connected at its ends to the two heads to permit rotational movement of at least one of the heads with respect to the annular body, at least one of the rotatable heads having a slot in its edge portion of sufficient radial depth to successively uncover an open end of each hole as the head is rotated with respect to the annular body, and a scale marked on the annular body and extending from end to end of the container holes for direct reading of hematocrit percent after centrifuging.

* * * * *